United States Patent
Dixon et al.

(10) Patent No.: US 12,274,613 B2
(45) Date of Patent: Apr. 15, 2025

(54) POLYMER COMPOSITE-COVERED STENTS

(71) Applicant: C. R. BARD, INC., Tempe, AZ (US)

(72) Inventors: Mathew Dixon, Mesa, AZ (US);
Albana Kosta, Scottsdale, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 840 days.

(21) Appl. No.: 14/582,074

(22) Filed: Dec. 23, 2014

(65) Prior Publication Data

US 2015/0223932 A1    Aug. 13, 2015

Related U.S. Application Data

(60) Provisional application No. 61/937,235, filed on Feb. 7, 2014.

(51) Int. Cl.
*A61F 2/24*        (2006.01)
*A61L 31/04*       (2006.01)
*A61L 31/14*       (2006.01)

(52) U.S. Cl.
CPC .......... *A61F 2/2418* (2013.01); *A61L 31/048* (2013.01); *A61L 31/14* (2013.01); *A61L 2420/08* (2013.01); *B32B 2250/24* (2013.01); *B32B 2307/514* (2013.01); *B32B 2535/00* (2013.01)

(58) Field of Classification Search
CPC ................................ B32B 5/26; A61F 2/2418
USPC ........................................ 428/304.4; 623/1.1
See application file for complete search history.

(56) References Cited

U.S. PATENT DOCUMENTS

| | | | | |
|---|---|---|---|---|
| 3,819,587 | A * | 6/1974 | Kwoleck | C08L 77/00 |
| | | | | 264/210.8 |
| 4,419,317 | A | 12/1983 | Fujiwara et al. | |
| 5,607,478 | A * | 3/1997 | Lentz | A61F 2/06 |
| | | | | 623/1.22 |
| 5,788,626 | A * | 8/1998 | Thompson | A61L 31/10 |
| | | | | 623/1.15 |
| 5,827,327 | A * | 10/1998 | McHaney | A61F 2/06 |
| | | | | 623/1.44 |
| 8,585,753 | B2 | 11/2013 | Scanlon et al. | |
| 2003/0040702 | A1* | 2/2003 | Wang | A61L 29/041 |
| | | | | 604/93.01 |
| 2003/0116260 | A1* | 6/2003 | Chobotov | A61F 2/07 |
| | | | | 156/217 |
| 2004/0038607 | A1 | 2/2004 | Williamson et al. | |
| 2005/0004664 | A1* | 1/2005 | Martakos | A61F 2/06 |
| | | | | 623/1.49 |
| 2006/0111771 | A1* | 5/2006 | Ton | A61F 2/962 |
| | | | | 623/1.15 |
| 2014/0316513 | A1* | 10/2014 | Tang | A61F 2/2418 |
| | | | | 623/1.16 |
| 2015/0196688 | A1* | 7/2015 | James | A61L 27/50 |
| | | | | 623/2.12 |

OTHER PUBLICATIONS

PCT/US2014/072289 filed Dec. 23, 2014 International Search Report dated Mar. 20, 2015.
PCT/US2014/072289 filed Dec. 23, 2014 Written Opinion dated Mar. 20, 2015.

* cited by examiner

*Primary Examiner* — Elizabeth M Imani
(74) *Attorney, Agent, or Firm* — Rutan & Tucker LLP

(57) ABSTRACT

Stent, stent coverings, and methods of making medical devices useful in vascular valves are disclosed. Stent coverings include layered, oriented, or calendered polymer films.

14 Claims, 7 Drawing Sheets

POLYMER COMPOSITE-COVERED STENTS

PRIORITY

This application claims priority to U.S. Application No. 61/937,235, filed Feb. 7, 2014, which is incorporated by reference in its entirety into this application.

BACKGROUND

Aortic stenosis is a common cause of valvular heart. Its incidence increases exponentially in older patients. Fibrosis, degeneration and subsequent calcification are no longer believed to be passive or purely degenerative in nature. Over time, as fibrosis and calcification worsens, valve leaflets become increasingly rigid, restricting their ability to open. This type of decreased function impedes blood flow through the heart causing hear failure, for example. Other causes of deformed and stenotic aortic valvular lesions include rheumatic heart disease, as well as congenital heart disease.

Heart valves change from their structure at birth driven in part by the normal dynamic daily stresses. But stenotic changes usually do not harm a person for many decades unless infection causes the stenosis. While the person lives with these changes unhampered for a long time, when intervention does become needed, the person has often become a poor surgical candidate for typical heart valve replacement using open heart techniques.

Minimally invasive valvuloplasty techniques can dilate stenosed valves using catheter balloons and catheter-placed replacement heart valves. During this procedure, a catheter having a deflated balloon is percutaneously inserted into a vein or artery and advanced until the balloon is positioned within the heart valve needing treatment. The balloon is then inflated to dilate the diseased valve opening, disrupting the rigid sheets of calcium permitting placement of the replacement valve. After the new valve has been placed, the balloon is deflated and removed from the patient's cardiovascular system.

Catheter-based cardiovascular procedures include TAVI (transcatheter aortic valve implantation), TAVR (transcatheter aortic valve replacement), and PAVR (percutaneous aortic valve replacement) devices.

Percutaneous aortic valve replacement (PAVR), transcatheter aortic valve Implantation (TAVI), or transcatheter aortic valve replacement (TAVR) are similar procedures for aortic valve replacement through blood vessels associated with the target valve. These procedures as opposed to valve replacement by open heart surgery are considered minimally invasive procedures. These procedures deliver the replacement valve using one of several access methods such as transfemoral (in the upper leg), transapical (through the wall of the heart), subclavian (beneath the collar bone) and direct aortic (through a minimally invasive surgical incision into the aorta).

SUMMARY

The embodiments described in this disclosure relate to polymer film coverings for stents such as for valves or aortic valves. Depending on the embodiment, the polymer films may be anisotropically aligned or calendered.

Some embodiments include an inner polymer layer comprising an anisotropic polymer and having an orientation direction; a mid-layer polymer film comprising an anisotropic polymer and having an orientation direction at an inner orientation angle to the inner polymer film; and an outer polymer film comprising an anisotropic polymer and having an orientation direction at an outer orientation angle to the mid-layer polymer film; and a medical device disposed between the mid-layer film and the outer polymer film. In these or other embodiments, 0 is less than or equal to the inner orientation angle, which is less than or equal to 90 or 80 is less than or equal to the inner orientation angle, which is less than or equal to 90. In these or other embodiments, 0 is less than or equal to the outer orientation angle, which is less than or equal to 90 or 80 is less than or equal to the outer orientation angle, which is less than or equal to 90.

The orientation of the polymer chains in some embodiments is aligned with the longitudinal axis of the medical device at an angle of $0 \leq angle \leq 90$. That is the polymer chains align parallel, perpendicular, or any angle in between.

In some embodiments, the polymer is ePTFE or a polymer exhibiting a node-and-fibril structure. Medical device embodiments include one or more of the oriented polymer layers comprising material exhibiting unilaterally oriented fibrils. In some embodiments, the polymer comprises elemental carbon. In various embodiments, the polymer films of medical devices have stitch retention range of 250-800 gF or 452-691 gF.

Additionally, embodiments of the invention include methods of making a medical device comprising the steps of mounting an inner polymer film on a mandrel; forming a calendered mid-layer film; mounting the mid-layer film on the inner polymer film; mounting a stent on the mid-layer film; mounting an outer polymer film on the stent; followed by heating to a temperature.

In some of these embodiments, forming comprises providing a calendaring machine comprising at least two members; one member configured to press against and roll along the other member during a cycle; providing an oriented polymer layer having an orientation direction; arranging one oriented polymer layer on a slip; covering the oriented polymer layer with a second slip; installing the slips in the calendaring machine; and cycling the machine. In these or other embodiments, the orientation is substantially perpendicular or substantially parallel to a longitudinal axis of the medical device.

DETAILED DESCRIPTION

The following description of several embodiments describes non-limiting examples that further illustrate the invention. No titles of sections contained herein, including those appearing above, are limitations on the invention, but rather they are provided to structure the illustrative description of the invention that is provided by the specification.

Unless defined otherwise, all technical and scientific terms used in this document have the same meanings that one skilled in the art to which the disclosed invention pertains would ascribe to them. The singular forms "a", "an", and "the" include plural referents unless the context clearly indicates otherwise. Thus, for example, reference to "fluid" refers to one or more fluids, such as two or more fluids, three or more fluids, etc. Any mention of an element includes that element's equivalents as known to those skilled in the art.

The features, aspects, and advantages of the invention will become more apparent from the following detailed description, appended claims, and accompanying drawings.

Figure 1:
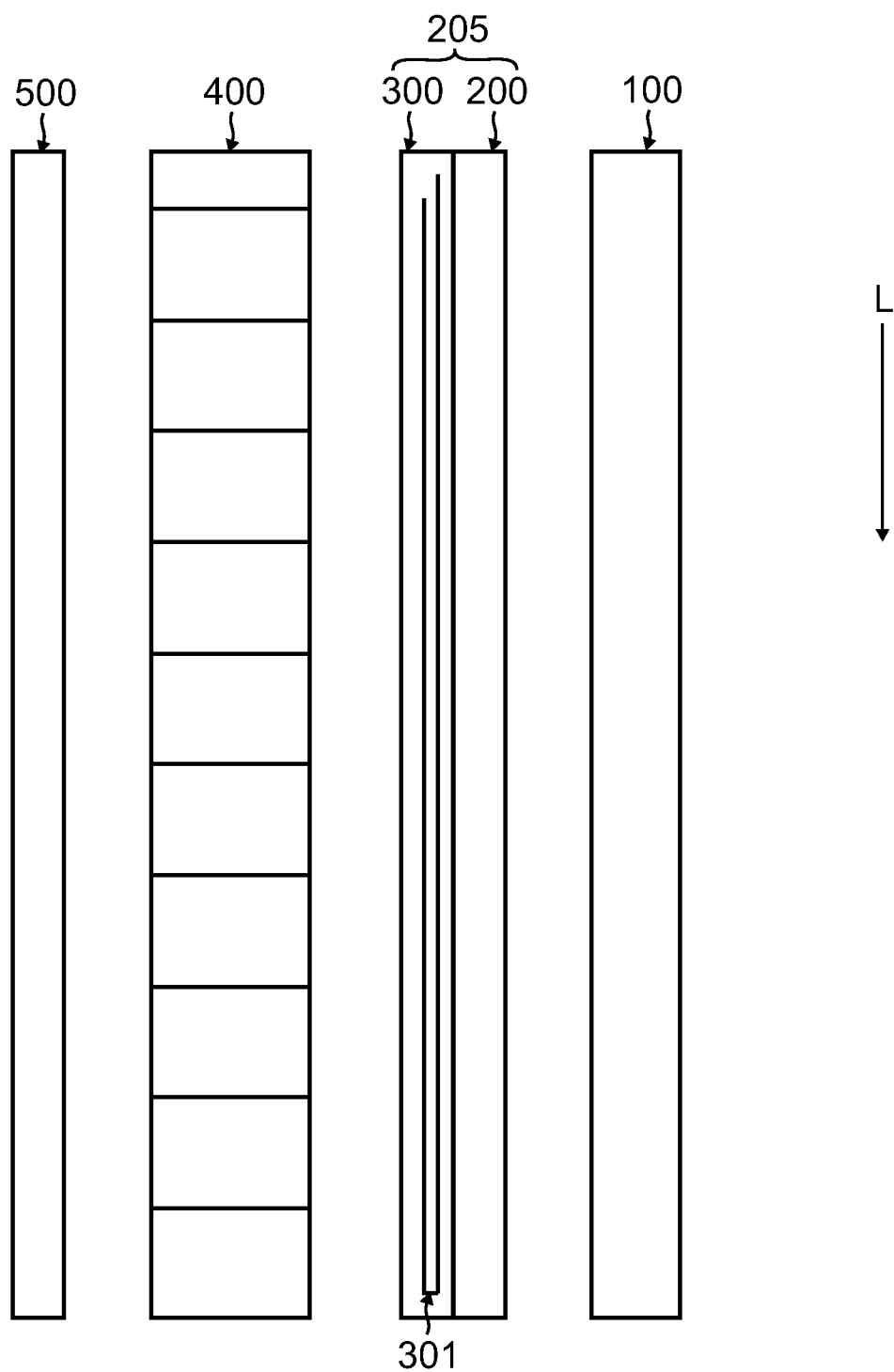
FIG. 1 is a schematic view of a portion of the valve of this invention.

FIG. 1 depicts a cross-sectional schematic view cut through the longitudinal axis of a medical device 50 of the current invention. Medical device 50 comprises a stent 400 or stent-like structure in which at least one polymer film 100, 200, 300 is disposed radially inward of stent 400 and at least one polymer film 500 is disposed radially outward of stent 400. One or more of the polymer film layers 100, 200, 300, or 500 comprise or can come from an oriented polymer film.

Figure 2:
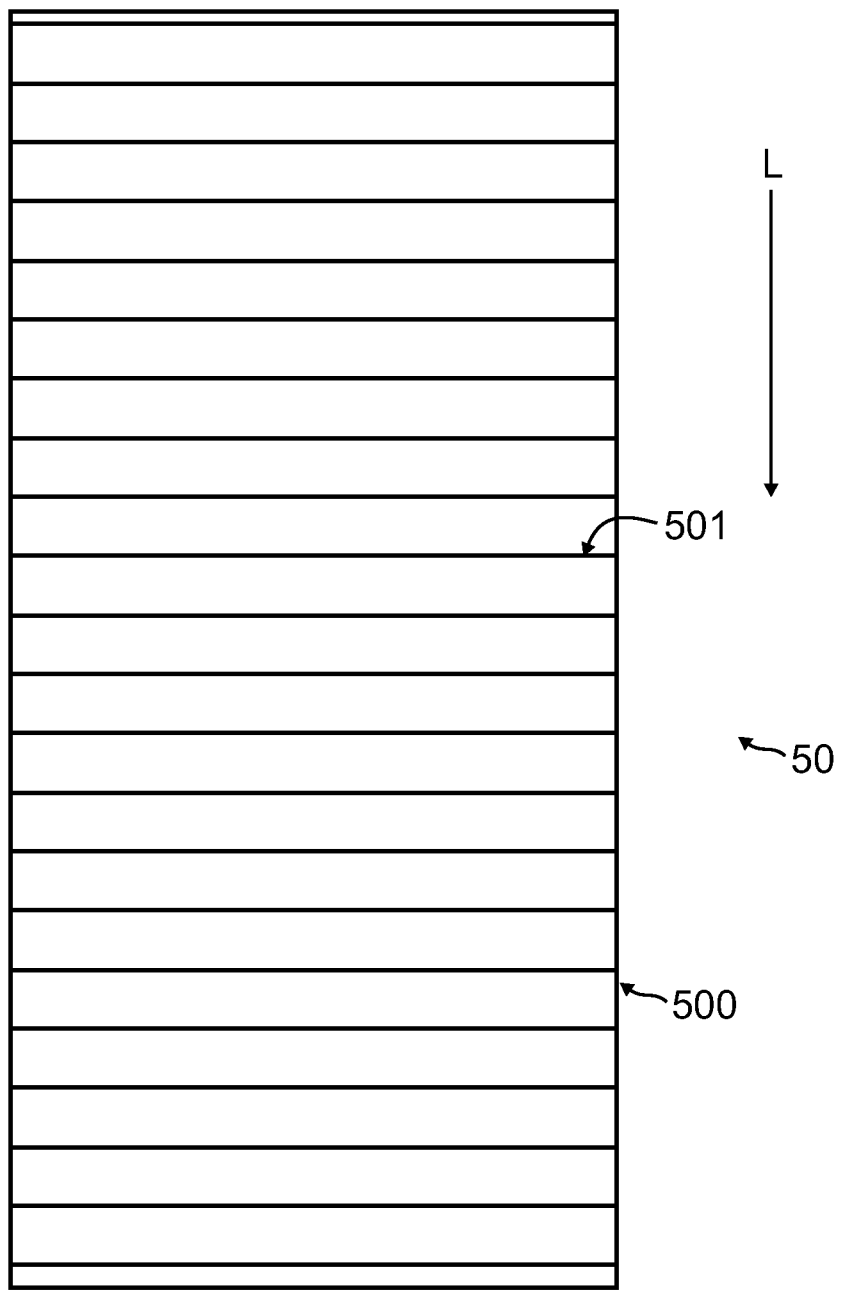
FIG. 2 is a schematic view of an outer layer of a valve of this invention.

Turning now to FIG. 2, the figure shows a schematic view of outer layer 500 of medical device 50. In this figure, a region of outer layer 500 is shown. For simplicity's sake, layer 500 is depicted as being flat rather than cylindrical. Vector L represents the medical device's longitudinal axis direction. As can be seen in the overly simplified depiction, polymer chains 501 tend to run in a direction perpendicular to vector L and hence to the device's longitudinal axis. In the cylindrical shape, the polymer chains would wrap around the medical device longitudinal axis, such that any given polymer chain would have generally the same longitudinal position along the polymer chain with respect to the medical device.

Figure 3:
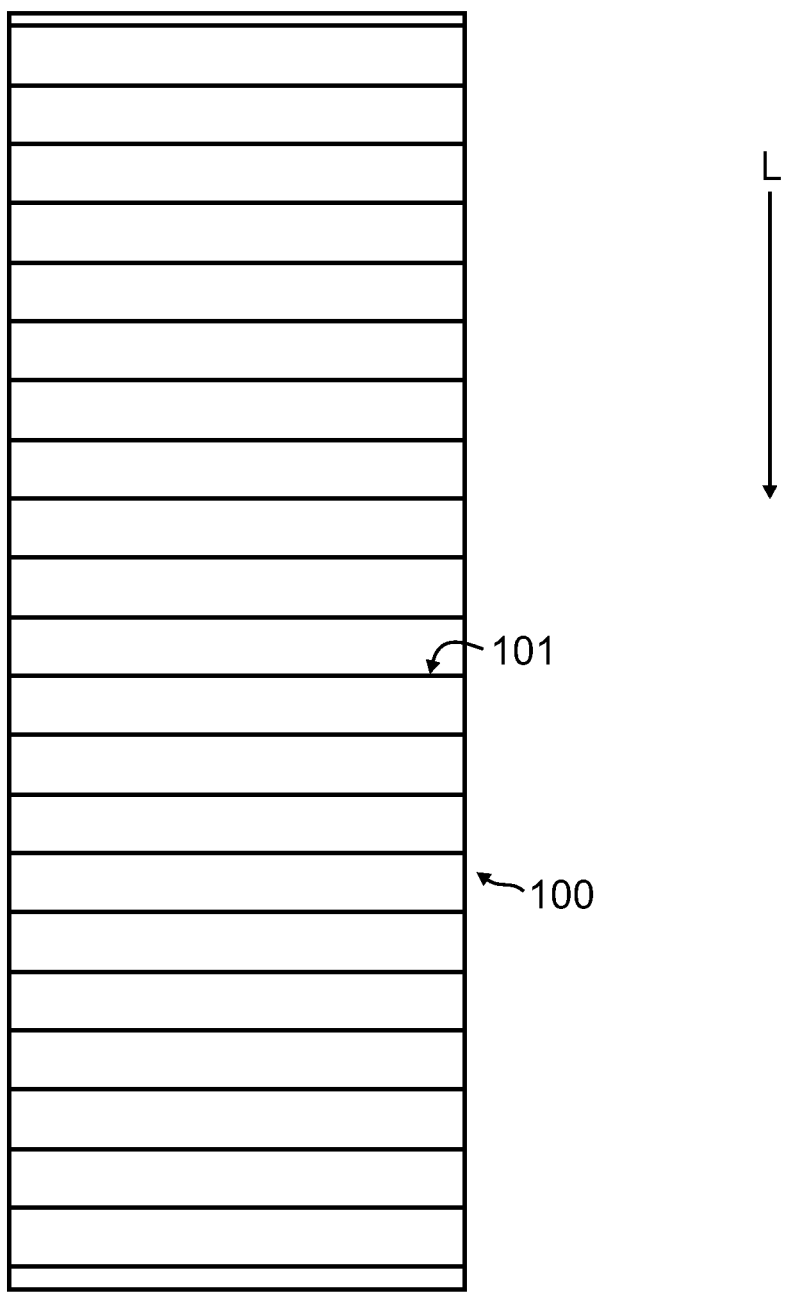
FIG. 3 is a schematic view of an inner layer of a valve of this invention.

Turning now to FIG. 3, the figure shows a schematic view of inner layer 100 of medical device 50. In this figure, a region of inner layer 100 is shown. For simplicity's sake, layer 100 is depicted as being flat rather than cylindrical. Vector L represents the medical device's longitudinal axis direction. As can be seen in the overly simplified depiction, polymer chains 101 tend to run in a direction perpendicular to vector L and hence to the device's longitudinal axis. In the cylindrical shape, the polymer chains would wrap around the medical device longitudinal axis, such that any given polymer chain would have generally the same longitudinal position along the polymer chain with respect to the medical device.

While FIGS. 2 and 3, depict an embodiment in which polymer chains 101 and 501 tend to run in a direction perpendicular to vector L, various other embodiments exist in which the orientation of inner layer 100, outer layer 500, or both have polymer chains 101 and 501 that tend to run in a direction perpendicular to vector L or embodiments where the polymer chains of either layer tend to run in a direction skew to vector L. For example, the angle of polymer chains 101 and 501 may be any angle between perpendicular and parallel to vector L.

Figure 4:
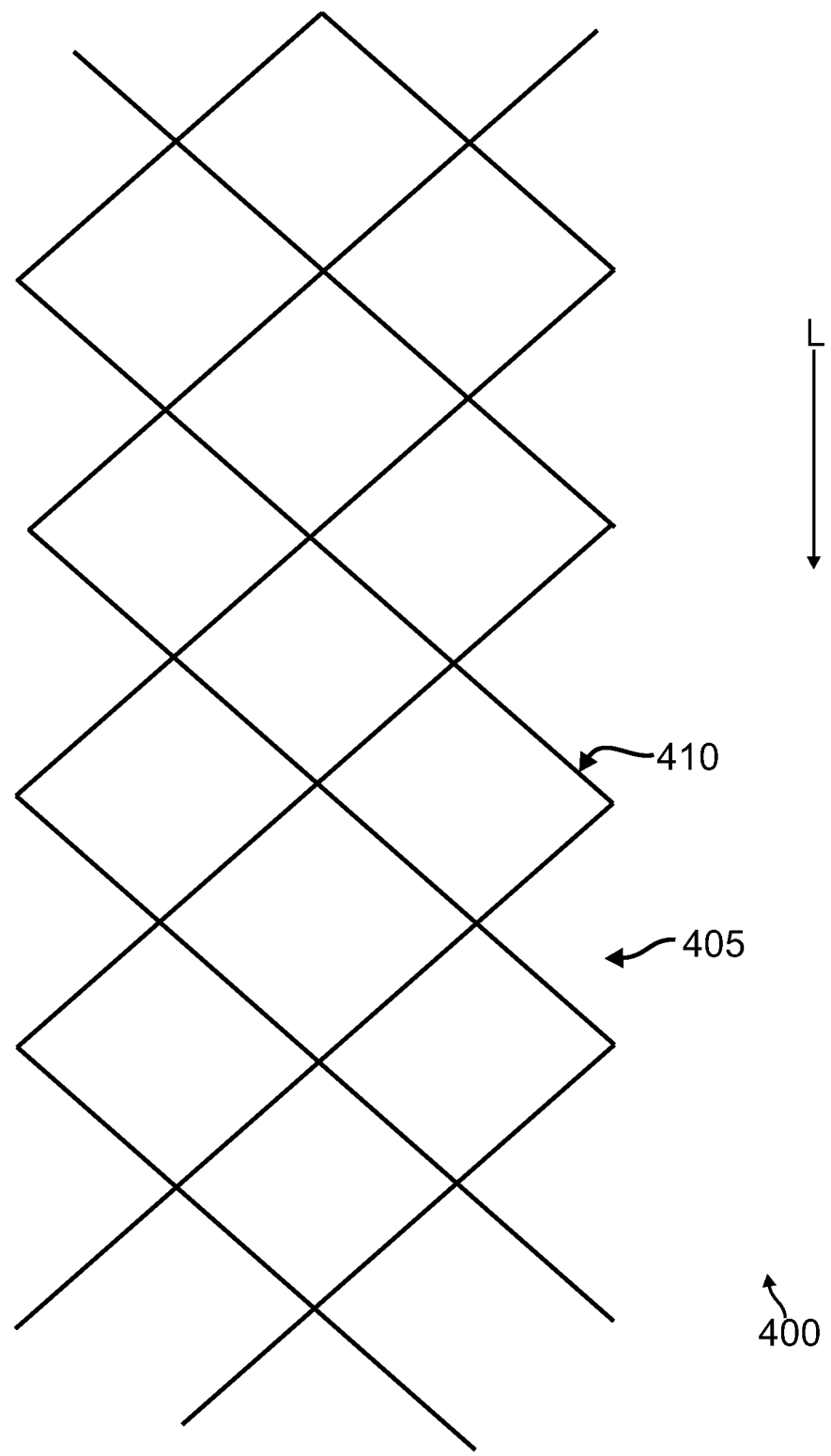
FIG. 4 is a schematic view of a stent or of a stent layer of this invention.

FIG. 4 depicts the stent or lattice-work structure 405 of stent 400. Struts 410 are shown. In this figure, a region of the stent or lattice-work structure 405. For simplicity's sake, structure 405 is depicted as being flat rather than cylindrical. For completeness sake, vector L is indicated in FIG. 4.

Figure 5:
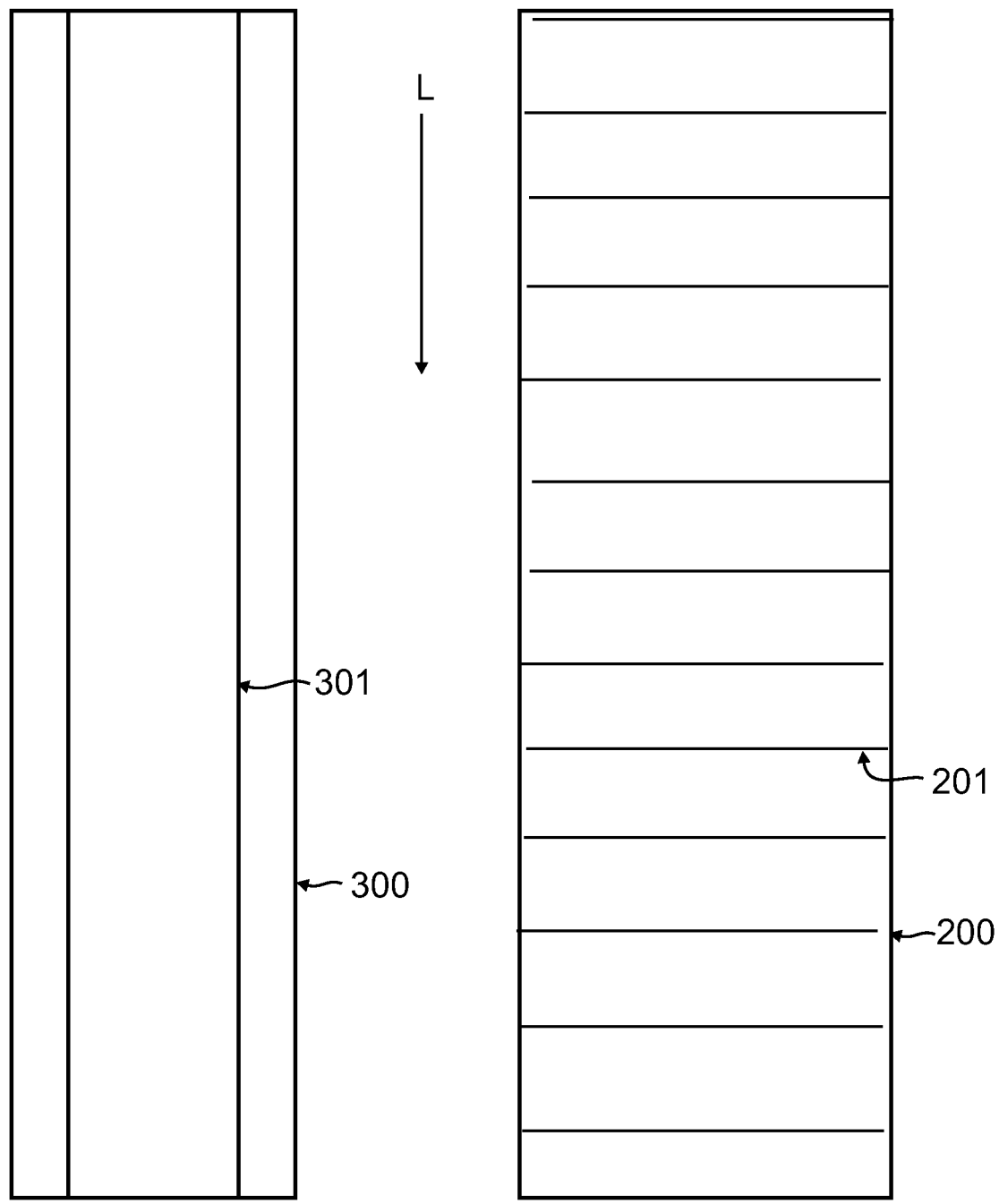
FIG. 5 is a schematic view of the mid layer of a valve of this invention.
Figure 6:
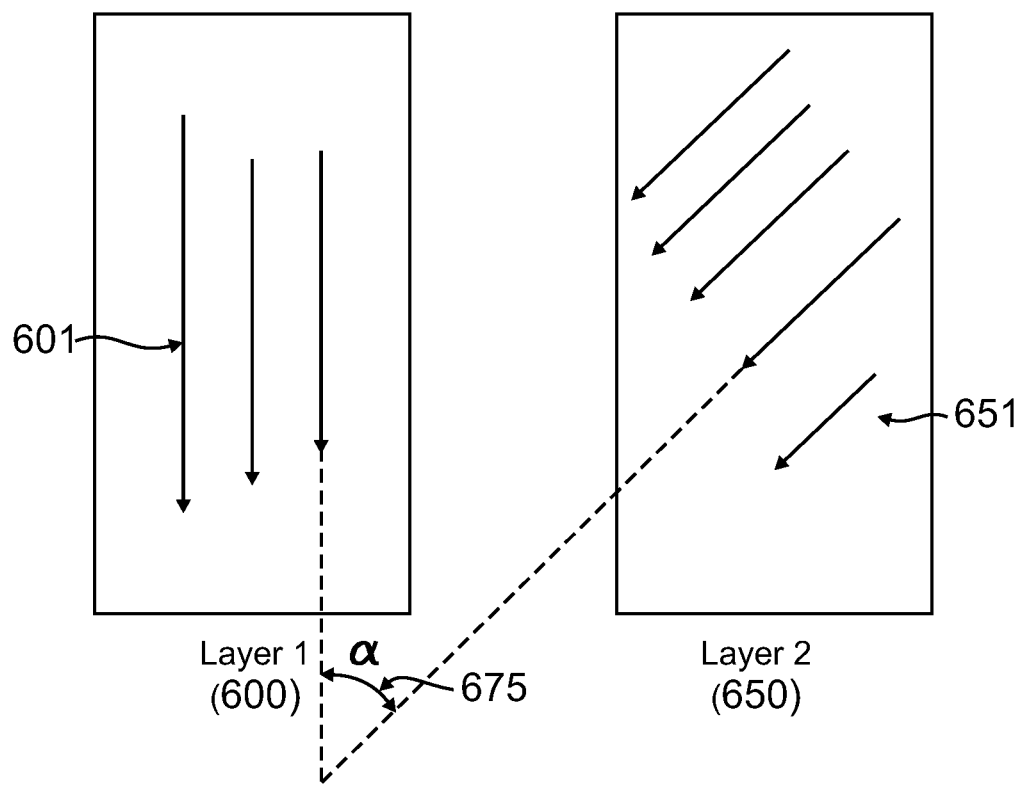
FIG. 6 is a view of polymer layers showing the definition of an orientation angle.

FIG. 5 depicts a mid-layer embodiment of the medical device 50. In this embodiment, the mid-layer comprises two layers 200, 300 that have polymer chain orientations 201, 301 in directions different from each other. Generally, the angle between the two orientation vectors is called an orientation or alignment angle. This orientation angle, a, is defined in FIG. 6. As can be seen in the figure, layer 1 (600) exhibits an orientation vector direction 601. And layer 2 (650) exhibits an orientation vector or direction 651. Angle α (675) is the angle between the orientation vectors.

The various layers of medical device 50 can have different compositions. Some embodiments employ a base material that is any one or any combination of expanded fluoroethylpolypropylene (ePTFE), polyamides, polyimides, silicones, fluoroethylpolypropylene (FEP), polypropylfluorinated amines (PFA), or other fluorinated polymers.

Some polymer materials useful in various embodiments of the invention include those described above, as well as anisotropic versions of those.

All materials useful in intervention monuments have thicknesses that range from 0.001 to 0.009 inches.

The stent portion can assume any known structure seen in the medical device arts. Stent-like devices useful in invention devices are any of those generally known to be useful in TAVI (transcatheter aortic valve implantation), TAVR (transcatheter aortic valve replacement), or PAVR (percutaneous aortic valve replacement) devices.

Percutaneous aortic valve replacement (PAVR), transcatheter aortic valve implantation (TAVI), or transcatheter aortic valve replacement (TAVR) are similar procedures for aortic valve replacement through blood vessels associated with the target valve. These procedures as opposed to valve replacement by open heart surgery are considered minimally invasive procedures. These procedures deliver the replacement valve using one of several access methods such as transfemoral (in the upper leg), transapical (through the wall of the heart), subclavian (beneath the collar bone) and direct aortic (through a minimally invasive surgical incision into the aorta).

Some embodiments employ examples of the above that are stainless steel or nitinol scaffolds (stents), sometimes with a biological valve attached directly to the metal structure or to a textile skirt sutured to the lower portion of the device. Inner diameters for stent-like devices range from 20 mm to 45 mm.

Exemplary construction of an exemplary stent graft, including exemplary ePTFE film production is provided herein.

Methods and techniques for expanding polytetrafluoroethylene have been known for many years. One of the earliest disclosures containing a discussion of such methods and resultant products is found in Japanese Patent No. 13,560/67 which was filed Nov. 1, 1963 and officially published on Aug. 1, 1967.

The basic process for expanding polytetrafluoroethylene is quite simple: The material is extruded into the desired geometric configuration. The material is then heated at a temperature below the sintering temperature of 327° C. and physically stretched or expanded along at least one axis. The expanded member is sintered by brief exposure to temperatures above 327° C., thereby crystallizing the expanded structure. As the raw extrudate is stretched, the non-porous polytetrafluoroethylene separates into solid nodes of polytetrafluoroethylene which remain structurally interconnected by polytetrafluoroethylene fibrils that are drawn from the nodes during expansion. Node size and distribution in the final product is adversely affected by very rapid expansion, uneven expansion, insufficient heating, non-uniform heating, and irregularly distributed expansion forces. The distance between nodes is directly proportional to the extent to which the extrudate has been expanded. When PTFE is properly expanded along one axis, virtually no dimensional changes are observed in the orthogonal direction. The expansion causes PTFE chains to orient in the expansion direction.

It has been found that the average internodular distance, as measured along the expansion direction, must fall within a relatively narrow range of values, between approximately 6 and 80 microns. One of ordinary skill in the art understands, the term "average" when used in conjunction with internodular distance and node size cannot be used or interpreted with statistical precision; rather, the term is intended to connote a nominal or typical dimension derived from a broad sample. By way of example, where the average internodular distance is said to be 30 microns, it would be expected that some of the nodes would be separated by only a few microns while others might be separated by 90 or 100 microns.

Various types of ePTFE are useful in embodiments of the invention. One type is referred to in this disclosure as Type-A ePTFE. This is a material prepared from carbon impregnated, unsintered PTFE.

This material has a node-and-fibril structure that is uniaxially oriented. Thus, Type-A ePTFE is a PTFE comprising elemental carbon exhibiting a node-and-fibril structure wherein the fibrils are substantially uniaxially aligned. Type-A material is also referred herein at MAT. A.

Another type of material is referred to in this disclosure as Type-B ePTFE. This is a material prepared from unsintered PTFE. This material has a node-and-fibril structure that is unilaterally oriented by expansion of the PTFE. Thus, Type-B ePTFE is a PTFE exhibiting a node-and-fibril structure wherein the fibrils are substantially unilaterally aligned. Type-B material is also referred herein as MAT. B.

As those of ordinary skill in the art recognize, an oriented polymer film is a polymer film in which individual polymer chains align in one or more specific directions. The polymer chains may align either be cause of their overall physical or chemical nature or because of processing steps that transform more or less randomly aligned polymer chains into chains that exhibit greater alignment directionality. For example, uniaxially oriented polymer chains align preferentially along one general direction. Similarly, biaxially oriented polymer chains align preferentially along two directions. Regardless of how or why the polymer chains align, a polymer with a specific chemical composition is a different material than a polymer with a similar chemical composition but with greater polymer chain alignment.

As one of ordinary skill in the art will recognize, this orientation does not mean that the polymer chains completely align. The orientation shows up as a distribution of chains with a non-random alignment of the chains. Some oriented polymers exhibit a structure akin to the node-and-fibril structure discussed above for ePTFE while other polymers exhibit structures that were derived from node-and-fibril structures. Yet others have no relationship to node-and-fibril structures.

A random alignment of polymer chains can also be called an isotropic arrangement. That is, a bulk sample of polymer chains with an isotropic orientation would exhibit chains substantially aligned equally in all directions. Conversely, a bulk sample of polymer chains can be anisotropically aligned or oriented and would therefore exhibit chain alignment that is not substantially equal in all directions. This disclosure refers to materials with an anisotropic distribution of chain directions as anisotropic polymers. "Anisotropic polymers" are polymers in which polymer chains align more in one direction than in others.

For purposes of this disclosure, orientation or alignment directions of the polymer chains are referenced against the medical device's longitudinal axis, which is present in all substantially cylindrical objects such as a stent or valve. A polymer orientation described as perpendicular (perp.) to the longitudinal axis would exhibit an alignment that is locally perpendicular to the longitudinal axis. Note that this local arrangement typically results in polymer chains tending to take an arcuate path around all or a portion of the cylindrical structure. Relatedly, parallel (para.) orientation means that the chains tend to run in a direction similar to that of the stent's longitudinal axis.

Both the parallel and the perpendicular directions are, of course, subject to more specific definition throughout this disclosure and are subject to the knowledge of one of ordinary skill in the art.

As discussed above, medical device 50 comprises at least inner and outer layers and optionally a mid-layer. In some embodiments, a polymer layer is calendered before it becomes part of an invention device.

Calendering is a process of treating a polymer film by exposing it to one or more pressure applications. These pressure applications use a mandrel plus a flat plate or a pad plus a flat plate to exert high pressure along the length of the film. In practice, the pressure application begins at one end of the film and progresses along the film from one end to the other. In some cases, calendering acts like a rolling pin flattening a pie crust. The film arrangement is such that pressure is applied along the z-axis considering the plane of the film as the x,y-plane. In some embodiments, a single film was calendered. In other embodiments, two films were calendered with one film layer, either partially or completely, on top of the other film layer, sometimes fusing the films together. The orientation angle between chains and such films ranges from 0 to 90° or 80 to 90°, in some embodiments.

In some embodiments, calendering permanently or semi-permanently reduces the film's thickness. In some embodiments, calendering obscures or destroys the node-and-fibril structure.

Figure 7:
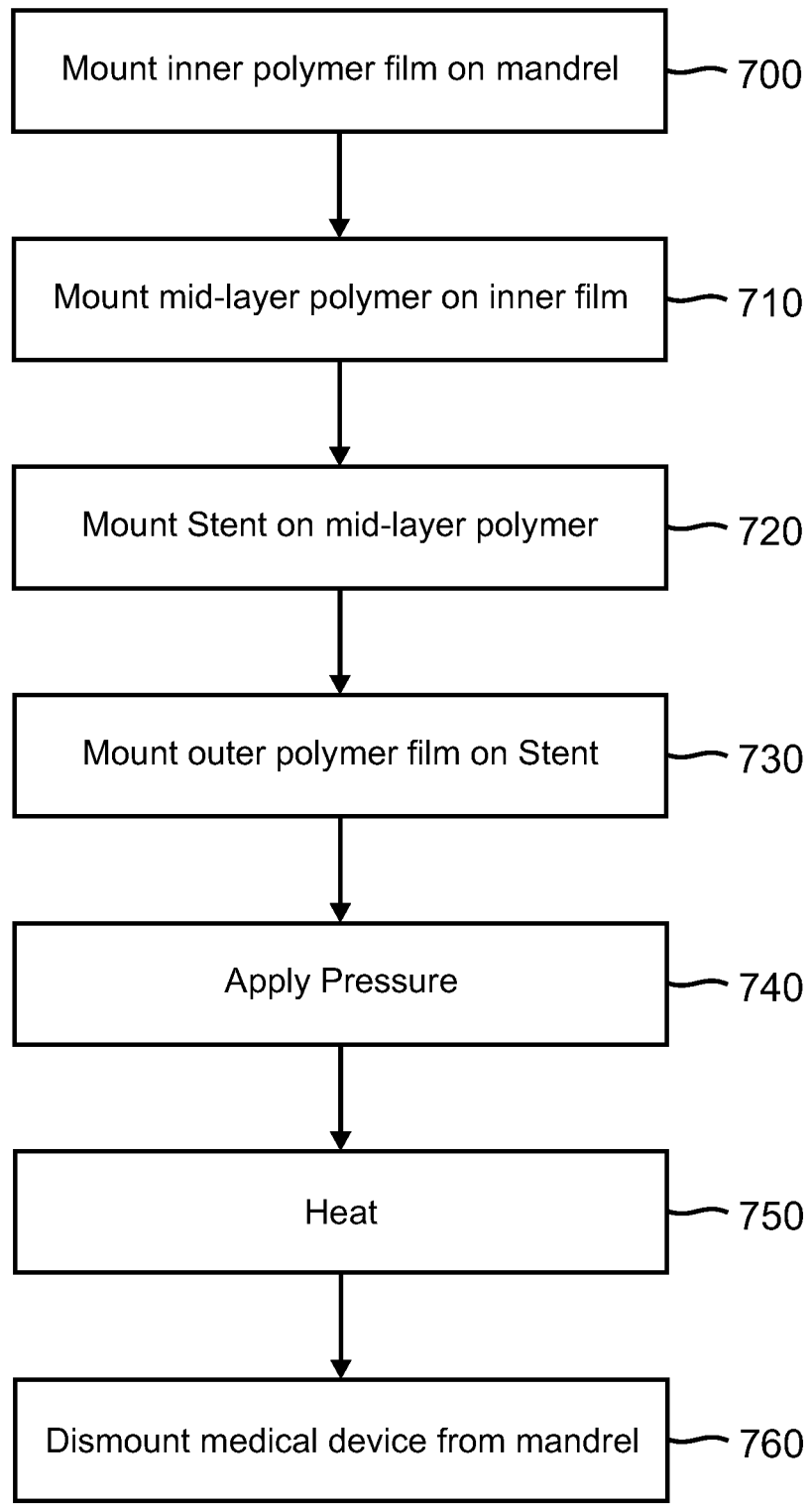
FIG. 7 is a flowchart showing a method of making a medical device.

FIG. 7 depicts a method for producing medical device 50. At step 700, mounting a polymer film occurs first. A film of a polymer is mounted on a mandrel. Different embodiments may employ isotropic or anisotropic polymer films. In the case of anisotropic polymer films, the orientation direction of the film can be arranged so that it is perpendicular, parallel, or skew to the longitudinal axis of the medical device by properly manipulating the film as it is mounted on the mandrel. Any number of inner layer films can be used.

At step 710, mounting a mid-layer polymer film 205 occurs next. Mid-layer polymer film 205 is mounted on the mandrel on top of inner layer 100. Mid-layer film 205 is typically mounted with similar constraints to those described for inner layer 100. In some embodiments of this mounting step, mid-layer film 205 covers inner layer 100; in other embodiments, mid-layer film 205 covers part of inner layer 100 film 100.

At step 720, mounting stent 400 on the mandrel occurs next. The nature of the stent was discussed above.

Ultimately, a step 730 of mounting outer polymer film layer 500 on the mandrel occurs. Outer polymer film 500 may completely cover stent 400 or may cover part of stent 400.

At step 740, the construction is placed under light to moderate, substantially uniform, pressure. In some embodiments, this construction is firmly wrapped with an inert tape such as PTFE to provide the pressure, among other things.

At step 750, the construction is heated to fuse polymer layers 100, 200, 300, 500 to each other, to stent 400, and around struts 410.

At step 760, after heating, the medical device is removed from the mandrel, which includes removing any inert tape.

In use, the medical device is delivered percutaneously through a patient's vasculature until the desired area for implanting the valve is reached. The decrease in valve thickness for medical device 50 allows for a decrease in the overall thickness of the delivery system and hence the diameter of the entry point. At that point, the clinician delivers the device by manipulation of a handle outside of the patient.

EXAMPLES

| Example | Inner Material/Orientation | Mid layer Material/Orientation | Outer Material/Orientation |
|---|---|---|---|
| Example 1 | 1 layer of MAT. A/Perp. | | 1 layer of MAT. A/Perp. |
| Example 2 | 2 layers of MAT. A/Perp. | | 4 layers of MAT. A/Perp. |
| Example 3 | 1 layer of MAT. A/Perp. | | Thicker Tube/Para. |
| Example 4 | 1 layer of MAT. A/Perp. | | 1 layer of MAT. A/Perp. |
| Example 5 | 1 layer of MAT. A/Perp. | Cal. MAT. A/Perp. | 1 layer of MAT. A/Perp. |
| Example 6 | 1 layer of MAT. A/Perp. | Cal. MAT. A/Perp. | 1 layer of MAT. A/Perp. |
| Example 7 | 1 layer of MAT. A/Perp. | Cal. MAT. A/Perp. | 1 layer of MAT. A/Perp. |
| Example 8 | 1 layer of MAT. A/Perp. | 2 layer 90° Cal. MAT. A/Perp. | 1 layer of MAT. A/Perp. |
| Example 9 | 1 layer of MAT. A/Perp. | 2 layer 45° Cal. MAT. A/Perp. | 1 layer of MAT. A/Perp. |
| Example 10 | 1 layer of MAT. A/Para. | 2 layer 90° Cal. MAT. A/Perp. | 1 layer of MAT. A/Perp. |
| Example 11 | 1 layer of MAT. A/Para. | 2 layer 45° Cal. MAT. A/Perp. | 1 layer of MAT. A/Perp. |
| Example 12 | 1 layer of MAT. A/Para. | 2 layer 90° Cal. MAT. A/Perp. | 1 layer of MAT. A/Perp. |
| Example 13 | 1 layer of MAT. A/Perp. | 2 layer 90° Cal. MAT. A/Perp. | 1 layer of MAT. A/Para. |
| Example 14 | 1 layer of MAT. A/Perp. | Textured 2 layer 90° Cal. MAT. A/Perp. | 1 layer of MAT. A/Para. |
| Example 15 | 1 layer of MAT. A/Perp. | 2 layer 90° Cal. MAT. A/Perp. | 1 layer of MAT. A/Para. |
| Example 16 | 1 layer of MAT. A/Perp. | 2 layer 90° Cal. MAT. A/Perp. | 1 layer of MAT. A/Para. |
| Example 17 | 1 layer of MAT. A/Perp. | 2 layer 90° Cal. MAT. A/Perp. | 1 layer of MAT. A/Para. |
| Example 18 | 1 layer of MAT. A/Perp. | 2 layer 90° Cal. MAT. A/Perp. | 1 layer of MAT. A/Para. |
| Example 19 | 1 layer of MAT. A/Perp. | 2 layer 90° Cal. MAT. A/Perp. | 1 layer of MAT. A/Para. |

MAT. A is the Type-A ePTFE, MAT. B is the Type-B ePTFE, Perp. is an orientation perpendicular to the longitudinal axis of the medical device, Para. is an orientation parallel to the longitudinal axis of the medical device, and Cal. indicates that the disclosed layer was calendered.

| Example | Stitch Holding Force gF | Bond Strength gF/mm |
|---|---|---|
| Example 1 | Approx. 250 | Approx. 19.31 (12.8-26.5) |
| Example 2 | Approx. 250 | Approx. 19.31 (12.8-26.5) |
| Example 3 | Approx. 250 | Approx. 19.31 (12.8-26.5) |
| Example 4 | Approx. 250 | Approx. 19.31 (12.8-26.5) |
| Example 5 | Approx. 691 (631-730) | Approx. 18.3 (13.1-21.2) |
| Example 6 | Approx. 637 (529-763) | Approx. 18.3 (13.1-21.2) |
| Example 7 | Approx. 637 (529-763) | Approx. 18.3 (13.1-21.2) |
| Example 8 | Approx. 549 (515-591) | Approx. 18.3 (13.1-21.2) |
| Example 9 | Approx. 606 (473-700) | Approx. 18.3 (13.1-21.2) |
| Example 10 | Approx. 502 (497-507) | Approx. 18.3 (13.1-21.2) |
| Example 11 | Approx. 452 (444-460) | Approx. 18.3 (13.1-21.2) |
| Example 12 | Approx. 502 (497-507) | Approx. 18.3 (13.1-21.2) |
| Example 13 | Approx. 502 (497-507) | Approx. 18.3 (13.1-21.2) |
| Example 14 | Approx. 502 (497-507) | Approx. 18.3 (13.1 21.2) |
| Example 15 | Approx. 502 (497-507) | Approx. 18.3 (13.1-21.2) |
| Example 16 | Approx. 502 (497-507) | Approx. 18.3 (13.1-21.2) |
| Example 17 | Approx. 502 (497-507) | Approx. 18.3 (13.1-21.2) |
| Example 18 | Approx. 502 (497-507) | Approx. 18.3 (13.1-21.2) |
| Example 19 | Approx. 502 (497-507) | Approx. 18.3 (13.1-21.2) |

Example 1

An inner layer formed from a graft of Material A was prepared by slicing the graft longitudinally and winding it onto a mandrel such that the original longitudinal axis of the graft was perpendicular to the longitudinal axis of the mandrel (and hence the resulting covered medical device). The layer was 0.115 mm plus or minus 0.035 mm thick.

A stent with a 26 mm expanded diameter was mounted on top of the inner layer.

An outer layer formed from a graft of Material A was prepared by slicing the graft longitudinally and winding it onto the mandrel on top of the stent such that the original longitudinal axis of the graft was perpendicular to the longitudinal axis of the mandrel (and hence the resulting covered medical device). The layer was 0.115 mm plus or minus 0.035 mm thick.

The entire assembly was wrapped with PTFE tape and heated to laminate the layers to each other, around the struts of the stent. The entire assembly was heated at 360° C. for 30 minutes.

Stitch retention was measured using the methods specified in ISO7198 yielding values of 250 gF. Bond strength was measured using the methods specified in ASTM D903 yielding values of 19.31 gF/mm (12.8-26.5 gF/mm).

Example 2

An inner layer formed from a graft of Material A was prepared by slicing the graft longitudinally and winding two layers of it onto a mandrel such that the original longitudinal axis of the graft was perpendicular to the longitudinal axis of the mandrel (and hence the resulting covered medical device). Each layer was 0.115 mm plus or minus 0.035 mm thick.

A stent with a 26 mm expanded diameter was mounted on top of the inner layer.

An outer layer formed from a graft of Material A was prepared by slicing the graft longitudinally and winding 4 layers of it onto the mandrel on top of the stent such that the original longitudinal axis of the graft was perpendicular to the longitudinal axis of the mandrel (and hence the resulting covered medical device). Each layer was 0.115 mm plus or minus 0.035 mm thick.

The entire assembly was wrapped with PTFE tape and heated to laminate the layers to each other, around the struts of the stent. The entire assembly was heated at 360° C. for 30 minutes.

Stitch retention was measured using the methods specified in ISO7198 yielding values of 250 gF. Bond strength was measured using the methods specified in ASTM D903 yielding values of 19.31 gF/mm (12.8-26.5) gF/mm.

Example 3

An inner layer formed from a graft of Material A was prepared by slicing the graft longitudinally and winding it onto a mandrel such that the original longitudinal axis of the graft was perpendicular to the longitudinal axis of the mandrel (and hence the resulting covered medical device). The layer was 0.115 mm plus or minus 0.035 mm thick.

A stent with a 26 mm expanded diameter was mounted on top of the inner layer.

An outer layer formed from a graft of Material A was prepared by slicing the graft longitudinally and winding it onto the mandrel on top of the stent such that the original longitudinal axis of the graft was perpendicular to the longitudinal axis of the mandrel (and hence the resulting covered medical device). The layer was 0.115 mm plus or minus 0.035 mm thick.

The entire assembly was wrapped with PTFE tape and heated to laminate the layers to each other, around the struts of the stent. The entire assembly was heated at 360° C. for 30 minutes.

Stitch retention was measured using the methods specified in ISO7198 yielding values of 250 gF. Bond strength was measured using the methods specified in ASTM D903 yielding values of 19.31 gF/mm (12.8-26.5) gF/mm.

Example 4

An inner layer formed from a graft of Material A was prepared by slicing the graft longitudinally and winding it onto a mandrel such that the original longitudinal axis of the graft was perpendicular to the longitudinal axis of the mandrel (and hence the resulting covered medical device). The layer was 0.115 mm plus or minus 0.035 mm thick.

A non-cylindrical device was mounted on top of the inner layer.

An outer layer formed from a graft of Material A was prepared by slicing the graft longitudinally and winding it onto the mandrel on top of the stent such that the original longitudinal axis of the graft was perpendicular to the longitudinal axis of the mandrel (and hence the resulting covered medical device). The layer was 0.115 mm plus or minus 0.035 mm thick.

The entire assembly was wrapped with PTFE tape and heated to laminate the layers to each other, around the struts of the stent. The entire assembly was heated at 360° C. for 30 minutes.

Stitch retention was measured using the methods specified in ISO7198 yielding values of 250 gF. Bond strength was measured using the methods specified in ASTM D903 yielding values of 19.31 gF/mm (12.8-26.5) gF/mm.

Example 5

An inner layer formed from a graft of Material A was prepared by slicing the graft longitudinally and winding it onto a mandrel such that the original longitudinal axis of the graft was perpendicular to the longitudinal axis of the mandrel (and hence the resulting covered medical device). The layer was 0.115 mm plus or minus 0.035 mm thick.

A mid-layer formed from a graft of Material A was prepared by slicing the graft longitudinally. The layer was subjected to a calendering process comprising laying a piece of the graft material onto a calendering pad so that it lays vertical. Next, a second calendering pad was place over the material forming a stack. Then, the stack was placed into a calendering machine and a calendering pin or member was placed on top of the stack. A calendering cycle (two rolls per pressure setting starting at 20 psi and ending at 60 psi with five pressure changes) was then initiated. The calendering cycle was repeated until a desired thickness of 0.025 mm was reached.

This calendered material was wound over the inner layer material such that the original longitudinal axis of the graft was perpendicular to the longitudinal axis of the mandrel.

A stent with a 26 mm expanded diameter was mounted on top of the inner layer.

An outer layer formed from a graft of Material A was prepared by slicing the graft longitudinally and winding it onto the mandrel on top of the stent such that the original longitudinal axis of the graft was perpendicular to the longitudinal axis of the mandrel (and hence the resulting covered medical device). The layer was 0.115 mm plus or minus 0.035 mm thick.

The entire assembly was wrapped with PTFE tape and heated to laminate the layers to each other, around the struts of the stent. The entire assembly was heated at 360° C. for 30 minutes.

Stitch retention was measured using the methods specified in ISO7198 yielding values of 691 gF (631-730) gf. Bond strength was measured using the methods specified in ASTM D903 yielding values of 18.3 gF/mm (13.1-21.2) gF/mm.

Example 6

An inner layer formed from a graft of Material A was prepared by slicing the graft longitudinally and winding it onto a mandrel such that the original longitudinal axis of the graft was perpendicular to the longitudinal axis of the mandrel (and hence the resulting covered medical device). The layer was 0.065 mm plus or minus 0.025 mm thick.

A mid-layer formed from a graft of Material A was prepared by slicing the graft longitudinally. The layer was subjected to a calendering process comprising laying a piece of the graft material onto a calendering pad so that it lays vertical. Next, a second calendering pad was place over the material forming a stack. Then, the stack was placed into a calendering machine and a calendering pin or member was placed on top of the stack. A calendering cycle (two rolls per pressure setting starting at 20 psi and ending at 60 psi with five pressure changes) was initiated, and the calendering cycle repeated until a desired thickness of 0.001 inches was reached.

A stent with a 26 mm expanded diameter was mounted on top of the inner layer.

An outer layer formed from a graft of Material A was prepared by slicing the graft longitudinally and winding it onto the mandrel on top of the stent such that the original longitudinal axis of the graft was perpendicular to the longitudinal axis of the mandrel (and hence the resulting covered medical device). The layer was 0.065 mm plus or minus 0.025 mm thick.

The entire assembly was wrapped with PTFE tape and heated to laminate the layers to each other, around the struts of the stent. The entire assembly was heated at 360° C. for 30 minutes.

Stitch retention was measured using the methods specified in ISO7198 yielding values of 637 gF (529-763). Bond strength was measured using the methods specified in ASTM D903 yielding values of 18.3 gF/mm (13.1-21.2) gF/mm.

Example 7

An inner layer formed from a graft of Material A was prepared by slicing the graft longitudinally and winding it onto a mandrel such that the original longitudinal axis of the graft was perpendicular to the longitudinal axis of the mandrel (and hence the resulting covered medical device). The layer was 0.065 mm plus or minus 0.025 mm thick.

A mid-layer formed from a graft of Material A was prepared by slicing the graft longitudinally. The layer was subjected to a calendering process comprising laying a piece of the graft material onto a calendering pad so that it lays vertical. Next, a second calendering pad was place over the material forming a stack. Then, the stack was placed into a calendering machine and a calendering pin or member was placed on top of the stack. A calendering cycle (two rolls per pressure setting starting at 20 psi and ending at 60 psi with five pressure changes) was initiated. The calendering cycle was repeated until a desired thickness of 0.0254 mm was reached.

A non-cylindrical nitinol stent with an expanded diameter of 26 mm was mounted on top of the inner layer.

An outer layer formed from a graft of Material A was prepared by slicing the graft longitudinally and winding it onto the mandrel on top of the stent such that the original longitudinal axis of the graft was perpendicular to the longitudinal axis of the mandrel (and hence the resulting covered medical device). The layer was 0.065 mm plus or minus 0.025 mm thick.

The entire assembly was wrapped with PTFE tape and heated to laminate the layers to each other, around the struts of the stent. The entire assembly was heated at 360° C. for 30 minutes.

Stitch retention was measured using the methods specified in ISO7198 yielding values of 637 gF 529-763) gf. Bond strength was measured using the methods specified in ASTM D903 yielding values of 18.3 gF/mm (13.1-21.2) gF/mm.

Example 8

An inner layer formed from a graft of Material A was prepared by slicing the graft longitudinally and winding it onto a mandrel such that the original longitudinal axis of the graft was perpendicular to the longitudinal axis of the mandrel (and hence the resulting covered medical device). The layer was 0.065 mm plus or minus 0.025 mm thick.

A mid-layer formed from a graft of Material A was prepared by slicing the graft longitudinally. The material was subjected to a calendering process comprising laying a first piece of the graft material onto a calendering pad so that it lays vertical. Next a second layer of material was placed over the first piece of graft material so that the orientation direction of the first layer of graft material was perpendicular to the second layer of graft material. This is called 2-layer, 90 degree calendering. Next, a second calendering pad was place over the materials forming a stack. Then the stack was placed into a calendering machine and a calendering pin or member was placed on top of the stack. A calendering cycle (two rolls per pressure setting starting at 20 psi and ending at 60 psi with five pressure changes) was initiated. The calendering cycle was repeated until a desired thickness of 0.001 inches was reached.

A stent with a 26 mm expanded diameter was mounted on top of the inner layer.

An outer layer formed from a graft of Material A was prepared by slicing the graft longitudinally and winding it onto the mandrel on top of the stent such that the original longitudinal axis of the graft was perpendicular to the longitudinal axis of the mandrel (and hence the resulting covered medical device). The layer was 0.065 mm plus or minus 0.025 mm thick.

The entire assembly was wrapped with PTFE tape and heated to laminate the layers to each other, around the struts of the stent. The entire assembly was heated at 360° C. for 30 minutes.

Stitch retention was measured using the methods specified in ISO7198 yielding values of 549 gF (515-591) gF.) Bond strength was measured using the methods specified in ASTM D903 yielding values of 18.3 gF/mm (13.1-21.2) gF/mm.

Example 9

An inner layer formed from a graft of Material A was prepared by slicing the graft longitudinally and winding it onto a mandrel such that the original longitudinal axis of the graft was perpendicular to the longitudinal axis of the mandrel (and hence the resulting covered medical device). The layer was 0.065 mm plus or minus 0.025 mm thick.

A mid-layer formed from a graft of Material A was prepared by slicing the graft longitudinally. The material was subjected to a calendering process comprising laying a first piece of the graft material onto a calendering pad so that it lays vertical. Next a second layer of material was placed over the first piece of graft material so that the orientation direction of the first layer of graft material made an angle of 45 degrees with the second layer of graft material. This is called 2-layer, 45 degree calendering. Next, a second calendering pad was place over the materials forming a stack. Then the stack was placed into a calendering machine and a calendering pin or member was placed on top of the stack. A calendering cycle (two rolls per pressure setting starting at 20 psi and ending at 60 psi with five pressure changes) was initiated, and repeated until a desired thickness of 0.001 inches was reached.

A stent with a 26 mm expanded diameter was mounted on top of the inner layer.

An outer layer formed from a graft of Material A was prepared by slicing the graft longitudinally and winding it onto the mandrel on top of the stent such that the original longitudinal axis of the graft was perpendicular to the longitudinal axis of the mandrel (and hence the resulting covered medical device). The layer was 0.065 mm plus or minus 0.025 mm thick.

The entire assembly was wrapped with PTFE tape and heated to laminate the layers to each other, around the struts of the stent. The entire assembly was heated at 360° C. for 30 minutes.

Stitch retention was measured using the methods specified in ISO7198 yielding values of 606 gF (473-700) gF. Bond strength was measured using the methods specified in ASTM D903 yielding values of 18.3 gF/mm (13.1-21.2) gF/mm.

Example 10

This medical device was prepared substantially the same way as the medical device of Example 8. The difference between this example and Example 8 is that in this example the inner layer was wound onto the mandrel such that the original longitudinal axis of the graft was parallel to the longitudinal axis of the mandrel (and hence the resulting covered medical device). The inner and outer layers were each 0.065 mm plus or minus 0.025" thick.

Stitch retention was measured using the methods specified in ISO7198 yielding values of 502 gF (497-507) gF. Bond strength was measured using the methods specified in ASTM D903 yielding values of 18.3 gF/mm (13.1-21.2) gF/mm.

Example 11

This medical device was prepared substantially the same way as the medical device of Example 9. The difference between this example and Example 9 is that in this example the inner layer was wound onto the mandrel such that the original longitudinal axis of the graft was parallel to the longitudinal axis of the mandrel (and hence the resulting covered medical device). The inner and outer layers were each 0.065 mm plus or minus 0.025" thick.

Stitch retention was measured using the methods specified in ISO7198 yielding values of 452 gF (444-460) gF. Bond strength was measured using the methods specified in ASTM D903 yielding values of 18.3 gF/mm (13.1-21.2) gF/mm.

Example 12

This medical device was prepared substantially the same way as the medical device of Example 10. The difference between this example and Example 10 is that in this example the outer layer was formed from a thicker graft. The outer layer was 0.115 mm plus or minus 0.035" thick. The inner layer was 0.065 mm plus or minus 0.025 mm thick.

Stitch retention was measured using the methods specified in ISO7198 yielding values of 502 gF (497-507) gF. Bond strength was measured using the methods specified in ASTM D903 yielding values of 18.3 gF/mm (13.1-21.2) gF/mm.

Example 13

This medical device was prepared substantially the same way as the medical device of Example 8. The difference between this example and Example 8 is that, in this example, the outer layer was formed from a thicker graft that was wound onto the mandrel on top of the stent such that the original longitudinal axis of the graft was parallel to the longitudinal axis of the mandrel (and hence the resulting covered medical device). The outer layer was 0.115 mm plus or minus 0.035 mm thick. The inner layer was 0.065 mm plus or minus 0.025 mm thick.

Stitch retention was measured using the methods specified in ISO7198 yielding values of 502 gF (497-507) gF. Bond strength was measured using the methods specified in ASTM D903 yielding values of 18.3 gF/mm (13.1-21.2) gF/mm.

Example 14

This medical device was prepared substantially the same way as the medical device of Example 13. The difference between this example and Example 13 is that, in this example, the mid-layer was formed using textured calendering pads.

Stitch retention was measured using the methods specified in ISO7198 yielding values of 502 gF (497-507) gF. Bond strength was measured using the methods specified in ASTM D903 yielding values of 18.3 gF/mm (13.1-21.2) gF/mm.

Example 15

This medical device was prepared substantially the same way as the medical device of Example 13. The difference between this example and Example 13 is that, in this example, the mid-layer was strategically placed so as to improve the bond between the inner and outer layers at the laser cut point.

Stitch retention was measured using the methods specified in ISO7198 yielding values of 502 gF (497-507) gF. Bond strength was measured using the methods specified in ASTM D903 yielding values of 18.3 gF/mm (13.1-21.2) gF/mm.

Example 16

This medical device was prepared substantially the same way as the medical device of Example 15. The difference between this example and Example 15 is that, in this example, the device included a skirt at the end thereof, which is an extension of the inner, outer, and calendered material.

Stitch retention was measured using the methods specified in ISO7198 yielding values of 502 gF (497-507) gF. Bond strength was measured using the methods specified in ASTM D903 yielding values of 18.3 gF/mm (13.1-21.2) gF/mm.

Example 17

This medical device was prepared substantially the same way as the medical device of Example 16. The difference between this example and Example 16 is that, in this example, the skirt at the end of the device includes a suture loop.

Stitch retention was measured using the methods specified in ISO7198 yielding values of 502 gF (497-507) gF. Bond strength was measured using the methods specified in ASTM D903 yielding values of 18.3 gF/mm (13.1-21.2) gF/mm.

Example 18

This medical device was prepared substantially the same way as the medical device of Example 16. The difference between this example and Example 16 is that, in this example, the skirt at the end of the device was reinforced with two layers of calendered material oriented 90°.

Stitch retention was measured using the methods specified in ISO7198 yielding values of 502 gF (497-507) gF. Bond strength was measured using the methods specified in ASTM D903 yielding values of 18.3 gF/mm (13.1-21.2) gF/mm.

Example 19

This medical device was prepared substantially the same way as the medical device of Example 13. The difference between this example and Example 13 is that instead of a stent, a non-cylindrical medical device with a 26 mm expanded diameter was mounted on top of the inner layer.

Stitch retention was measured using the methods specified in ISO7198 yielding values of 502 gF (497-507) gF. Bond strength was measured using the methods specified in ASTM D903 yielding values of 18.3 gF/mm (13.1-21.2) gF/mm.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true, intended, explained, disclose, and understood scope and spirit of this invention's multitudinous embodiments and alternative descriptions.

Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. Accordingly, any combination of the various aspects, including features, components, configurations, orientations, etc. of the disclosed exemplary embodiments are intended to be within the scope of the present disclosure. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

The invention claimed is:

1. A heart valve replacement device, comprising:
a heart valve comprising:
a polymer composite including:
an inner anisotropic polymer layer having an inner-layer orientation;
an outer anisotropic polymer layer having an outer-layer orientation; and
a stent structure disposed between the inner anisotropic polymer layer and the outer anisotropic polymer layer, wherein:
at least one of the inner-layer orientation or the outer-layer orientation is perpendicular to a longitudinal axis of the stent structure,
the polymer composite is fused together around struts of the stent structure from a proximal end of the stent structure to a distal end of the stent structure, and
the polymer composite has an average stitch retention strength of at least about 250 gram-force (gF).

2. The heart valve replacement device according to claim 1, wherein both the inner-layer orientation and the outer-layer orientation are perpendicular to the longitudinal axis of the stent structure.

3. The heart valve replacement device according to claim 2, wherein both the inner anisotropic polymer layer and the outer anisotropic polymer layer comprise carbon-impregnated, unsintered, expanded polytetrafluoroethylene ("ePTFE").

4. The heart valve replacement device according to claim 1, wherein the polymer composite further includes a medial layer comprising one or more calendered anisotropic-polymer layers between the inner anisotropic polymer layer and the outer anisotropic polymer layer, and wherein the stent structure is disposed between the medial layer and the outer anisotropic polymer layer.

5. The heart valve replacement device according to claim 4, wherein the medial layer is a single calendered anisotropic polymer layer having a medial-layer orientation, and wherein the inner-layer orientation, the medial-layer orientation, and the outer-layer orientation are perpendicular to the longitudinal axis of the stent structure.

6. The heart valve replacement device according to claim 5, wherein the inner anisotropic polymer layer, the medial layer, and the outer anisotropic polymer layer comprise carbon-impregnated, unsintered, expanded polytetrafluoroethylene ("ePTFE").

7. The heart valve replacement device according to claim 5, wherein the polymer composite has the average stitch retention strength of at least about 637 gram-force (gF).

8. The heart valve replacement device according to claim 4, wherein the medial layer is two calendered anisotropic polymer layers oriented 90° to each other.

9. The heart valve replacement device according to claim 8, wherein both the inner-layer orientation and the outer-layer orientation are perpendicular to the longitudinal axis of the stent structure.

10. The heart valve replacement device according to claim 8, wherein the inner-layer orientation is perpendicular to the longitudinal axis of the stent structure, and wherein the outer-layer orientation is parallel to the longitudinal axis of the stent structure.

11. The heart valve replacement device according to claim 8, wherein the inner-layer orientation is parallel to the longitudinal axis of the stent structure, and wherein the outer-layer orientation is perpendicular to the longitudinal axis of the stent structure.

12. The heart valve replacement device according to claim 4, wherein the medial layer is two calendered anisotropic polymer layers oriented 45° to each other.

13. The heart valve replacement device according to claim 12, wherein both the inner-layer orientation and the outer-layer orientation are perpendicular to the longitudinal axis of the stent structure.

14. The heart valve replacement device according to claim 12, wherein the inner-layer orientation is parallel to the longitudinal axis of the stent structure, and wherein the outer-layer orientation is perpendicular to the longitudinal axis of the stent structure.

* * * * *